(12) United States Patent
Furrer et al.

(10) Patent No.: US 9,411,939 B2
(45) Date of Patent: Aug. 9, 2016

(54) METHOD FOR PRODUCING PATIENT-SPECIFIC PLATE

(71) Applicant: DePuy Synthes Products, Inc., Raynham, MA (US)

(72) Inventors: André Furrer, Oberdorf (CH); Timo Zillig, Mohlin (CH); Andrew Charles Davison, West Chester, PA (US); Razvan A. Gheorghe, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 361 days.

(21) Appl. No.: 13/801,244

(22) Filed: Mar. 13, 2013

(65) Prior Publication Data

US 2014/0074438 A1 Mar. 13, 2014

Related U.S. Application Data

(60) Provisional application No. 61/699,938, filed on Sep. 12, 2012.

(51) Int. Cl.
G06F 17/50 (2006.01)
G06F 19/00 (2011.01)
A61B 17/80 (2006.01)
A61B 17/00 (2006.01)
A61B 17/56 (2006.01)

(52) U.S. Cl.
CPC ........ *G06F 19/3437* (2013.01); *A61B 17/8071* (2013.01); *A61B 2017/00526* (2013.01); *A61B 2017/568* (2013.01); *A61B 2034/102* (2016.02)

(58) Field of Classification Search
CPC G06F 19/3437; A61B 17/8071; A61B 19/50; A61B 2019/508; A61B 2019/502; A61B 2017/00526; A61B 2017/568
USPC .............................................. 703/1
See application file for complete search history.

(56) References Cited

U.S. PATENT DOCUMENTS

| 5,042,983 A | 8/1991 | Rayhack |
| 5,098,383 A | 3/1992 | Hemmy et al. |
| 5,176,685 A | 1/1993 | Rayhack |
| 5,413,579 A | 5/1995 | Tom Du Toit |
| 5,601,563 A | 2/1997 | Burke et al. |
| 5,860,981 A | 1/1999 | Bertin et al. |
| 5,876,204 A * | 3/1999 | Day et al. ...................... 433/173 |
| 5,916,220 A | 6/1999 | Masini |

(Continued)

FOREIGN PATENT DOCUMENTS

| EP | 0468192 | 9/1996 |
| EP | 1216666 | 6/2002 |

(Continued)

OTHER PUBLICATIONS

International Patent Application No. PCT/US2013/030139: International Search Report dated Aug. 6, 2013, 19 pages.

(Continued)

*Primary Examiner* — Dwin M Craig
(74) *Attorney, Agent, or Firm* — Baker & Hostetler LLP

(57) ABSTRACT

A method of making a patient specific surgical orthopedic implant includes obtaining a virtual model of the orthopedic implant that is configured to fit over a particular tissue body, and virtually designing holes of the orthopedic implant.

28 Claims, 6 Drawing Sheets

(56) References Cited

U.S. PATENT DOCUMENTS

| | | | |
|---|---|---|---|
| 6,007,537 | A | 12/1999 | Burkinshaw et al. |
| 6,077,266 | A | 6/2000 | Medoff |
| 6,110,177 | A | 8/2000 | Ebner et al. |
| 6,978,188 | B1 | 12/2005 | Christensen |
| 7,621,919 | B2 | 11/2009 | Williams, III et al. |
| 7,758,345 | B1 * | 7/2010 | Christensen .................. 433/214 |
| 8,086,336 | B2 | 12/2011 | Christensen |
| 8,177,822 | B2 | 5/2012 | Medoff |
| 8,439,926 | B2 | 5/2013 | Bojarski et al. |
| 8,725,465 | B2 | 5/2014 | Hultgren et al. |
| 8,775,133 | B2 | 7/2014 | Schroeder |
| 2002/0082604 | A1 | 6/2002 | Abdelgany et al. |
| 2002/0138078 | A1 | 9/2002 | Chappuis |
| 2004/0034361 | A1 | 2/2004 | Dalton |
| 2004/0097946 | A1 | 5/2004 | Dietzel et al. |
| 2005/0043835 | A1 | 2/2005 | Christensen |
| 2005/0133955 | A1 | 6/2005 | Christensen |
| 2008/0195240 | A1 * | 8/2008 | Martin et al. .................. 700/98 |
| 2008/0221569 | A1 | 9/2008 | Moore et al. |
| 2008/0275452 | A1 | 11/2008 | Lang et al. |
| 2009/0047165 | A1 | 2/2009 | Syvanen et al. |
| 2009/0082774 | A1 | 3/2009 | Oti et al. |
| 2009/0087276 | A1 | 4/2009 | Rose |
| 2009/0088758 | A1 | 4/2009 | Bennett |
| 2009/0092948 | A1 * | 4/2009 | Gantes .......................... 433/215 |
| 2010/0137873 | A1 | 6/2010 | Grady, Jr. et al. |
| 2010/0152782 | A1 | 6/2010 | Stone et al. |
| 2010/0168752 | A1 | 7/2010 | Edwards |
| 2010/0168753 | A1 | 7/2010 | Edwards et al. |
| 2010/0169057 | A1 | 7/2010 | Hultgren et al. |
| 2010/0216083 | A1 | 8/2010 | Grobbee |
| 2010/0262150 | A1 | 10/2010 | Lian |
| 2010/0292963 | A1 | 11/2010 | Schroeder |
| 2010/0324558 | A1 | 12/2010 | Bickley et al. |
| 2011/0008754 | A1 * | 1/2011 | Bassett et al. ................. 433/175 |
| 2011/0092804 | A1 | 4/2011 | Schoenefeld et al. |
| 2011/0144698 | A1 | 6/2011 | Buchbinder et al. |
| 2012/0022604 | A1 | 1/2012 | Polley et al. |
| 2012/0029574 | A1 | 2/2012 | Furrer et al. |
| 2012/0109135 | A1 | 5/2012 | Bailey |
| 2012/0130686 | A1 | 5/2012 | Graumann |
| 2012/0141034 | A1 | 6/2012 | Iannotti et al. |
| 2012/0150243 | A9 | 6/2012 | Crawford et al. |
| 2012/0261848 | A1 * | 10/2012 | Haraszati ....................... 264/17 |
| 2012/0276509 | A1 | 11/2012 | Iannotti et al. |
| 2012/0289965 | A1 | 11/2012 | Gelaude et al. |
| 2012/0303131 | A1 | 11/2012 | Chana |
| 2013/0072988 | A1 | 3/2013 | Hulliger |

FOREIGN PATENT DOCUMENTS

| | | |
|---|---|---|
| EP | 1854611 | 11/2007 |
| EP | 1808137 | 4/2010 |
| EP | 2208470 | 7/2010 |
| EP | 2062224 | 8/2010 |
| FR | 2847453 | 5/2004 |
| WO | WO 2004/039266 | 5/2004 |
| WO | WO 2005/032790 | 4/2005 |
| WO | WO 2011/070367 | 6/2011 |
| WO | WO 2011/071611 | 6/2011 |
| WO | WO 2011/080260 | 7/2011 |
| WO | WO 2011/103689 A1 | 9/2011 |
| WO | WO 2012/027574 | 3/2012 |

OTHER PUBLICATIONS

U.S. Appl. No. 13/792,746, filed Mar. 11, 2013, Davison et al.

U.S. Appl. No. 13/792,849, filed Mar. 11, 2013, Davison et al.

Cevidanes et al., "Three-Dimensional Surgical Simulation", Am. J. Orthod. Dentofacial. Orthop., Sep. 2010, 138(3), 361-371.

Chapuis et al., "A New System for Computer-Aided Preoperative Planning and Intraoperative Navigation During Corrective Jaw Surgery", IEEE Trans. Inf. Technol. Biomed., May 2007, 11(3), 274-287.

DePuy Orthopaedics, Inc., "TruMatch Personalized Solutions", Oct. 27, 2011, 2 pages.

International Patent Application No. PCT/US2013/030131: International Search Report dated Jun. 25, 2013, 11 pages.

International Patent Application No. PCT/US2013/030139: Invitation to Pay Additional Fees dated Jun. 10, 2013, 5 pages.

Lubbers et al., "Surgical Navigation in Craniomaxillofacial Surgery: Expensive Toy or Useful Tool? A Classification of Different Indications", J. Oral Maxillofac. Surg., Jan. 2011, 69(1), 300-308.

Mavili et al., "Use of Three-Dimensional Medical Modeling Methods for Precise Planning of Orthognathic Surgery", J. Craniofac. Surg., Jul. 2007, 18(4), 740-747.

Olszewski et al., "Innovative Procedure for Computer-Assisted Genioplasty: Three-Dimensional Cephalometry, Rapid-Prototyping Model and Surgical Splint", Int. J. Oral Maxillofac. Surg., Jul. 2010, 39(7), 721-724.

International Patent Application No. PCT/US2013/059226: International Search Report dated Dec. 2, 2013, 10 pages.

U.S. Appl. No. 13/900,817, filed May 23, 2013, Davison et al.

Klein et al., A Computerized Tomography (CT) Scan Appliance for Optimal Presurgical and Preprosthetic Planning of the Implant Patient, Practical Periodontics & Aesthetic Dentistry, vol. 5, No. 6, 1993, 33-39.

* cited by examiner

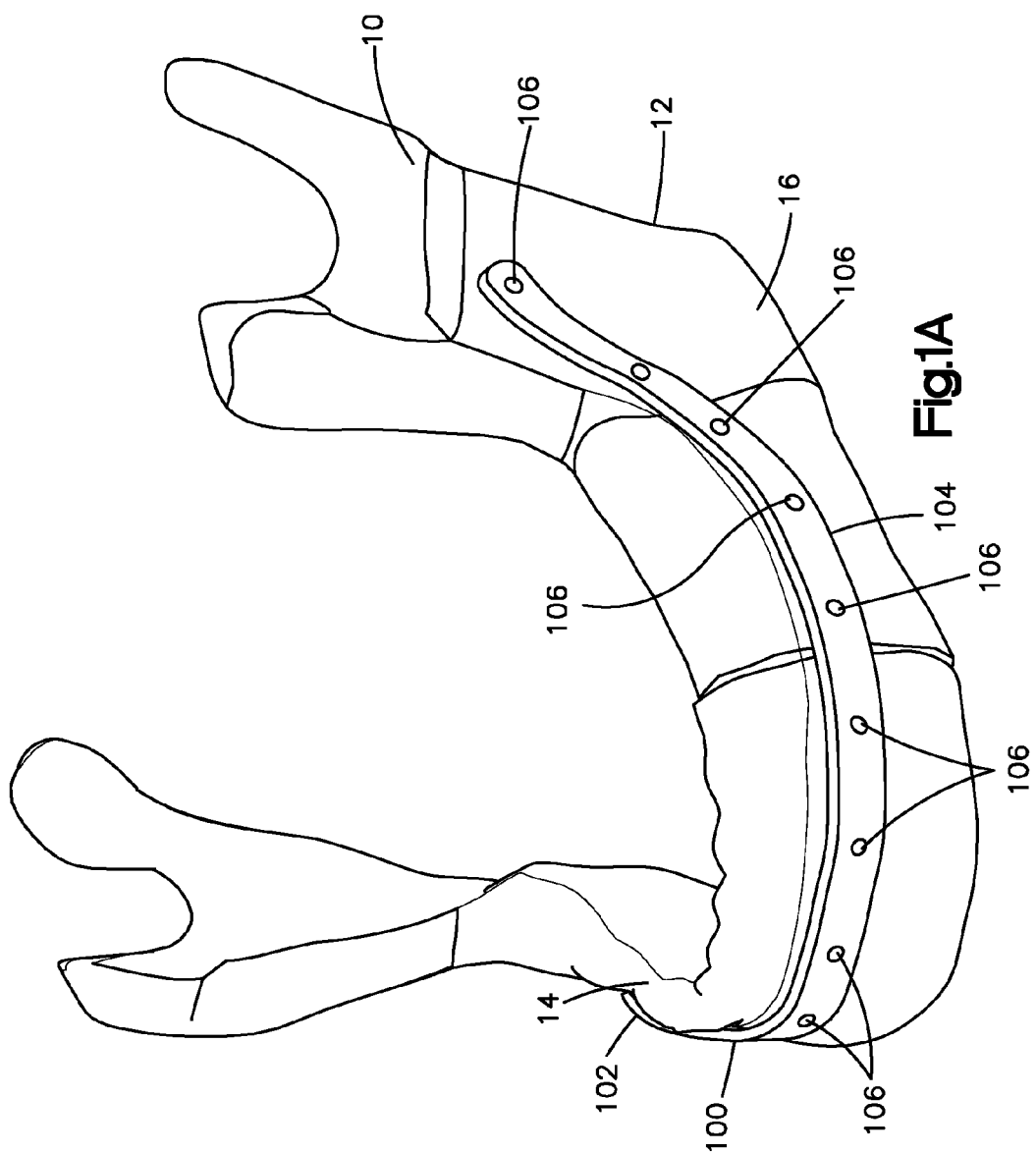

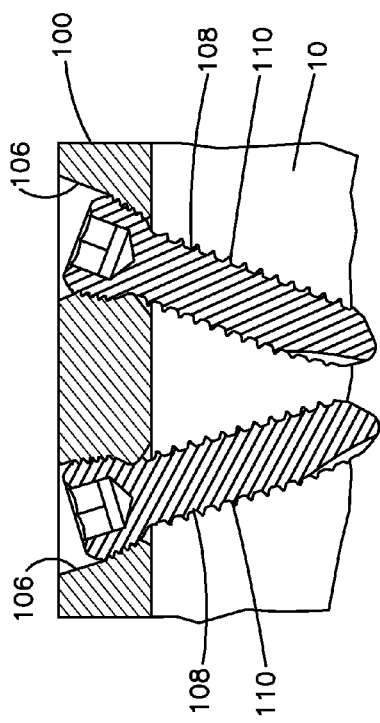
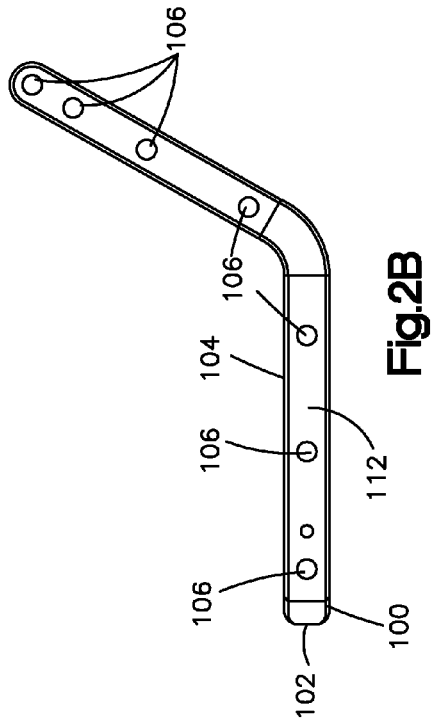
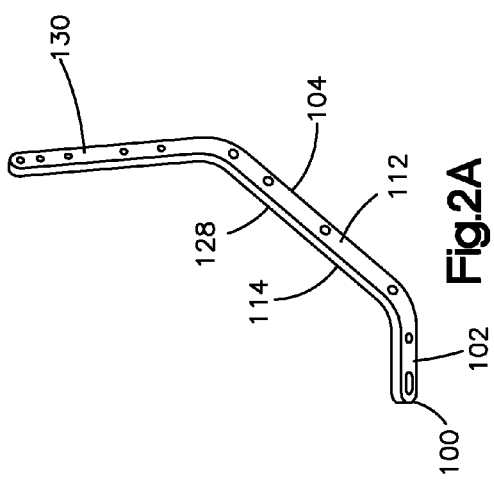

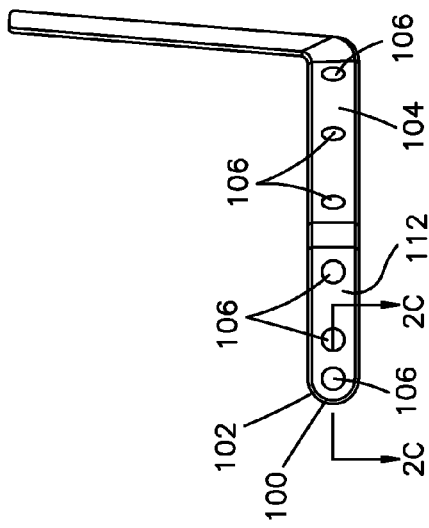
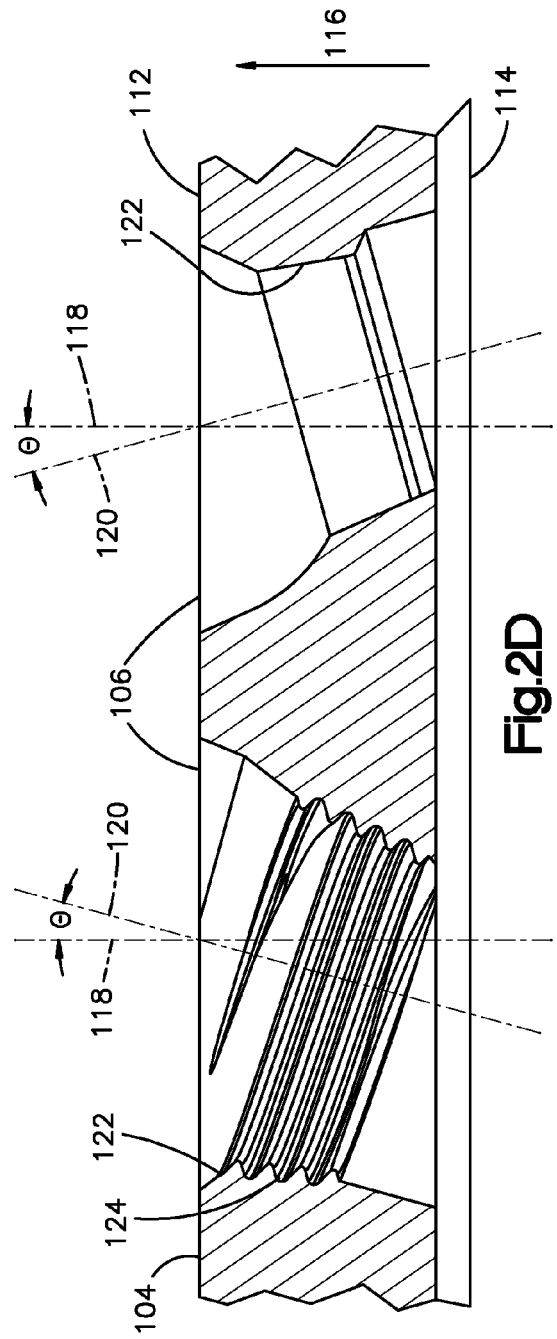

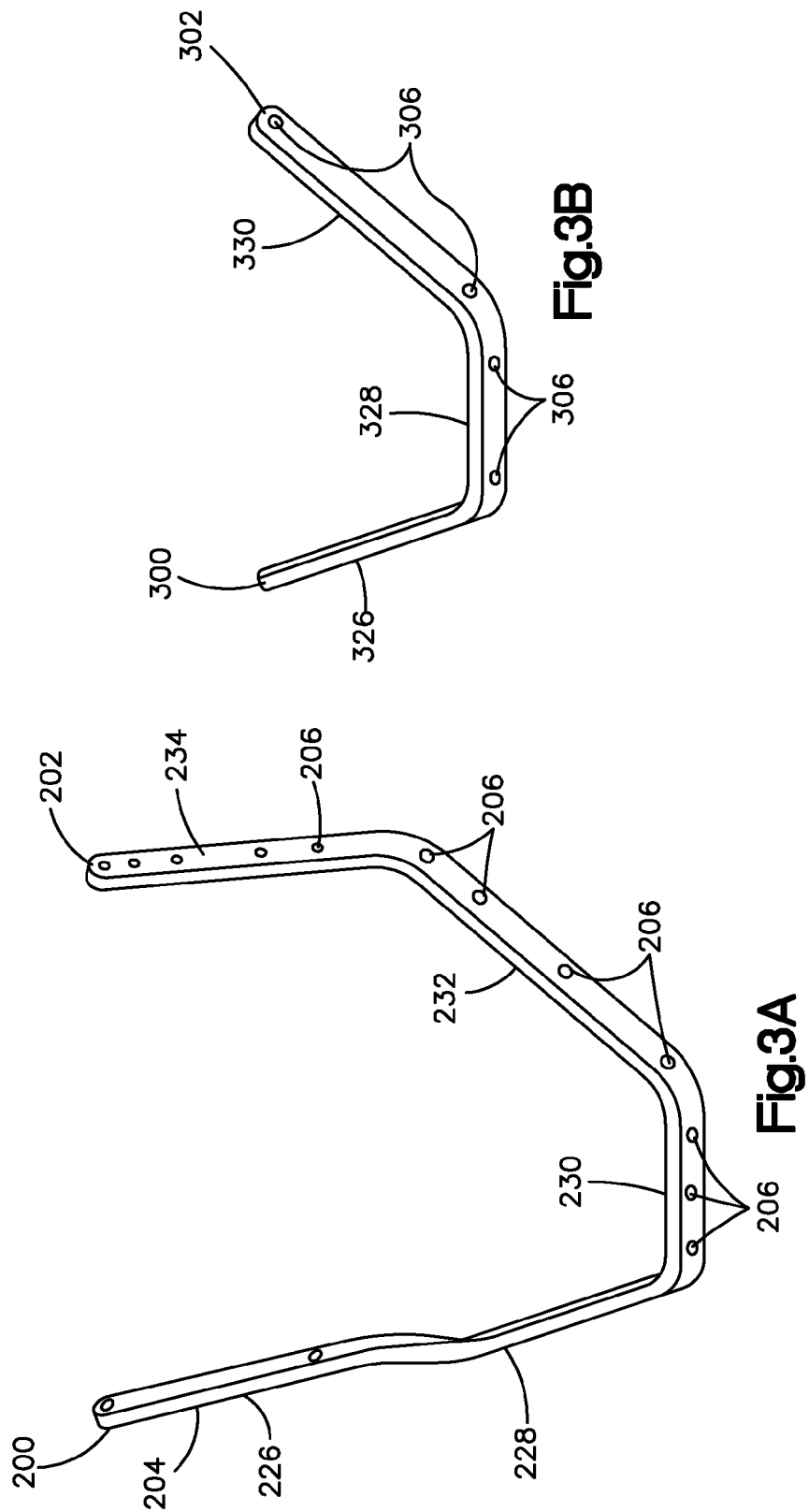

METHOD FOR PRODUCING PATIENT-SPECIFIC PLATE

CROSS-REFERENCE TO RELATED APPLICATIONS

This claims the benefit of U.S. Patent Application Ser. No. 61/699,938 filed Sep. 12, 2012, the disclosure of which is hereby incorporated by reference as if set forth in its entirety herein.

TECHNICAL FIELD

The present disclosure generally relates to methods and systems for producing orthopedic implants, and more particularly, to methods and systems for manufacturing patient-specific mandible plates.

BACKGROUND

Many surgical procedures involve the fixation of orthopedic implants, such as mandible plates, to a bone or a bone graft. One or more fasteners, such as bone screws, can be used to fix the orthopedic implant to the bone or bone graft. Some orthopedic implants include implant holes that are configured to receive fasteners. As such, these orthopedic implants can be attached to the bone or bone graft by inserting a fastener through each implant hole and into the bone or bone graft. However, it is important that the fasteners do not contact certain areas of the bone. For instance, in mandibular reconstruction, the fasteners should not contact nerves, teeth, and/or dental implants to avoid damaging the nerves, the teeth, the dental implant or any other hardware. It is also important that the fasteners do not interfere with each other when inserted through the implant holes of the orthopedic implant. Therefore, it is desirable to adjust the angulation of the implant holes such that the fasteners do not interfere with each other and do not contact specific tissue portions such as the nerves and teeth. The location and orientation of the nerves and teeth of each patient may vary. Accordingly, it is desirable to produce orthopedic implants that are specifically designed for a particular patient in order to adjust the angulation of the implant holes.

SUMMARY

The present disclosure relates to methods of making a patient specific orthopedic implant using, among other things, a computing device running a computer-aided software. In an embodiment, the method includes one or more of the following steps: (a) obtaining a virtual three-dimensional model of a tissue body; (b) designing a virtual three-dimensional model of an orthopedic implant that includes an implant body such that the virtual three-dimensional model of the orthopedic implant is contoured to fit over a particular portion of the virtual three-dimensional model of the tissue body; and (c) designing at least one hole that extends through the implant body such that at least one hole is positioned or angled with respect to the implant body so that a virtual three-dimensional model of a fastener does not extend into a predetermined section of the virtual three-dimensional model of the tissue body when the virtual three-dimensional model of the fastener is at least partially disposed in at least one hole.

In another embodiment, the method includes one or more of the following steps: (a) designing a virtual three-dimensional model of an orthopedic implant that is contoured to fit over a predetermined portion of a virtual three-dimensional model of a tissue body, the virtual three-dimensional model of the orthopedic implant including an implant body; and (b) creating at least one virtual hole that extends through the implant body of the virtual three-dimensional model of the orthopedic implant such that at least one virtual hole is positioned or angled relative to the implant body so that a virtual three-dimensional model of a fastener extends into a predetermined section of a virtual three-dimensional model of the tissue body when the virtual three-dimensional model of the fastener is at least partially disposed in at least one hole.

BRIEF DESCRIPTION OF THE DRAWINGS

The foregoing summary, as well as the following detailed description of the preferred embodiments of the application, will be better understood when read in conjunction with the appended drawings. For the purposes of illustrating the surgical instruments and methods of the present application, there is shown in the drawings preferred embodiments. It should be understood, however, that the application is not limited to the specific embodiments and methods disclosed, and reference is made to the claims for that purpose. In the drawings:

FIG. 1A is a perspective view of a mandible and a patient specific orthopedic implant that is coupled to the mandible, the orthopedic implant defining a plurality of holes, each of the holes configured and sized to receive a fastener;

FIG. 1D is an enlarged cross-sectional view of a portion orthopedic implant shown in FIG. 1C, taken around section 1D of FIG. 1C;

FIG. 2A is a perspective view of the patient specific orthopedic implant shown in FIG. 1A;

FIG. 2B is a side view of the patient specific orthopedic implant shown in FIG. 2A;

FIG. 2C is a front view of the patient specific orthopedic implant shown in FIG. 2A;

FIG. 2D is an enlarged cross-sectional view of the patient specific orthopedic implant shown in FIG. 2A, taken along section line 2C-2C of FIG. 2C;

FIG. 3A is a perspective view of a patient specific orthopedic implant in accordance with another embodiment of the present disclosure;

FIG. 3B is a perspective view of a patient specific orthopedic implant in accordance with yet another embodiment of the present disclosure.

DETAILED DESCRIPTION OF ILLUSTRATIVE EMBODIMENTS

Figure 1B:
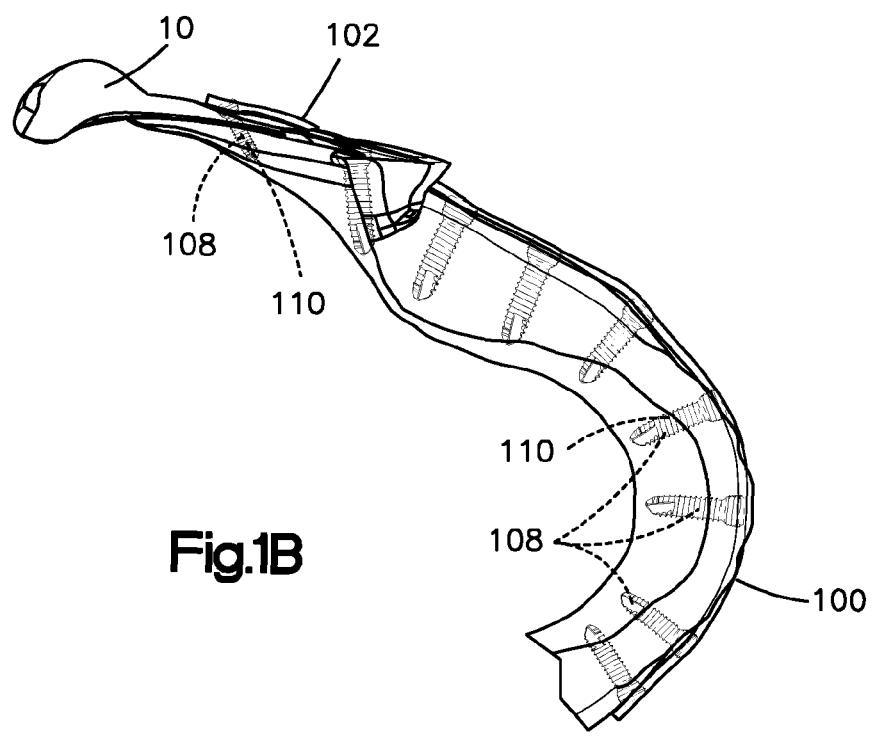
FIG. 1B is a top transparent view of a portion of the mandible and the orthopedic implant shown in FIG. 1A, showing fasteners inserted through at least some of the holes and into the mandible.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical device. The words, "anterior", "posterior", "superior", "inferior" and related words and/or phrases designate preferred positions and orientations in the human body to which reference is made and are not meant to be limiting. The terminology includes the above-listed words, derivatives thereof, and words of similar import.

Figure 1C:
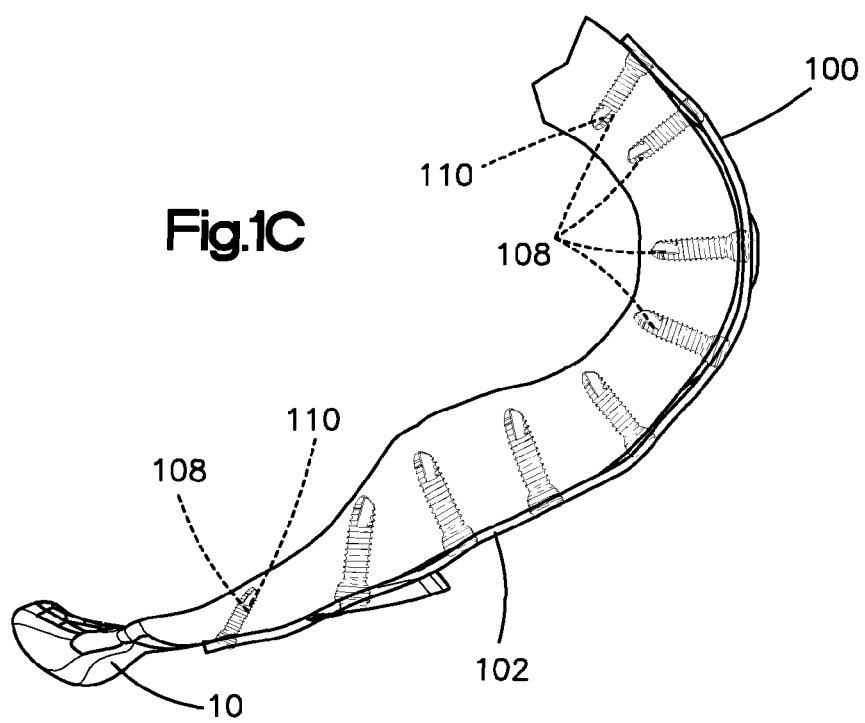
FIG. 1C is a bottom transparent view of the portion of the mandible and the orthopedic implant shown in FIG. 1B.

With reference to FIGS. 1A-C, a surgical system may include a patient specific orthopedic implant 100 that is configured to be coupled to a tissue body 10 of a patient. The surgical system may further include one or more fasteners 108 that are configured to couple the patient specific orthopedic implant 100 to the tissue body 10. One or more fasteners 108 can be configured as bone screws 110. Regardless of its configuration, each fastener 108 is configured and sized to be inserted in one of the holes 106 and into the tissue body 10 so as to fix the patient specific orthopedic implant 100 to the tissue body 10. The patent specific orthopedic implant 100 can be contoured to fit over a particular portion of the tissue body 10 of a specific patient. As used herein, the tissue body 10 may include a patient's bone such as a mandible 16. Although the drawings show the mandible 16, the tissue body 10 can be other parts of the patient's anatomy such the maxilla.

The patient specific orthopedic implant 100 can be used to fix a first tissue segment 12 of the tissue body 10 to a second tissue segment of the tissue body 10. The first tissue segment 12 may be separated from the second tissue segment by a defect or diseased tissue portion. The defect may be, for example, a fracture. Thus, the first tissue segment 12 can be separated from the second tissue segment 14 by a fracture. The fixation of the first tissue segment 12 and the second tissue segment 14 can promote healing of the tissue body 10. Hence, the patient specific orthopedic implant 100 can support and hold the first tissue segment 12 relative to the second tissue segment 13 while osteogenesis occurs. Alternatively, the patient specific orthopedic implant 100 can be used to fix a bone graft to the first tissue segment 12 and the second tissue segment 14. In such case, a diseased portion of the tissue body 10 may be removed from the patient and replaced with the bone graft. The orthopedic implant 100 can then be used to fix the bone graft to the first tissue segment 12 and the second tissue segment 14. In particular, the bone graft may separate the first tissue segment 12 from the second tissue segment 14. Thus, the patient specific orthopedic implant 100 can support and hold the bone graft relative to the first tissue segment 12 and the second tissue segment 14.

The patient specific orthopedic implant 100 and various of its components are described herein in with reference to orthogonal direction components. That is, various parts of the orthopedic implant 100 can extend along a longitudinal direction L, a lateral direction A, and a transverse direction T. The transverse direction T may be substantially perpendicular to the lateral direction A and the longitudinal direction L. Unless otherwise specified herein, the terms "lateral," "longitudinal," and "transverse" are used to describe the orthogonal directional components of the various parts of the patient specific orthopedic implant 100. When the patient specific orthopedic implant 100 is coupled to the tissue body 10, the transverse direction T extends along the caudal-cranial direction of the patient, the lateral direction A extends along the medial-lateral direction of the patient, and the longitudinal direction L extends along the anterior-posterior direction of the patient.

With reference to FIGS. 2A-C, the patient specific orthopedic implant 100 can be configured as a bone plate 102 and includes an implant body 104 that can be partly or entirely made from any suitable biocompatible material. Suitable biocompatible materials include, but are not limited to, cobalt chromium molybdenum (CoCrMo), titanium, and titanium alloys, stainless steel, ceramics, or polymers such as polyetheretherketone (PEEK), polyetherketoneketone (PEKK), and bioresorbable materials. A coating may be added or applied to the implant body 104 to improve physical or chemical properties or to provide medications. Examples of coatings include plasma-sprayed titanium coating or Hydroxyapatite.

The implant body 104 defines an outer implant surface 112 and an opposed inner implant surface 114. The inner implant surface 114 can be spaced from the outer implant surface 112 along an axial direction 116. Since the implant body 104 may not have a completely planar configuration, the axial direction 116 may be different along different parts of the implant body 104. The thickness of the implant body 104 may be defined from the outer implant surface 112 to the inner implant surface 114 along the axial direction 116. Accordingly, the implant body 104 may define one or more thickness axes 118 that extend between the inner implant surface 114 and the outer implant surface 112. The thickness axis 118 may be substantially perpendicular to the inner implant surface 114 and the outer implant surface 112. The inner implant surface 114 can be contoured to match the contour of a particular outer surface of the tissue body 10 so that the patient specific orthopedic implant 100 can only fit over the that particular outer surface of the tissue body 10.

The patient specific orthopedic implant 100 defines one or more holes 106 that extend through the implant body 104 between the inner implant surface 114 and the outer implant surface 112 (FIG. 2A). Each of the holes 106 can be configured and sized to receive one of the fasteners 108 (FIG. 1B). In operation, one fastener 108 can be inserted through the hole 106 and into the tissue body 10 to couple the patient specific orthopedic implant 100 to the tissue body 10. The holes 106 may be elongate a hole axis 120 that extends between inner implant surface 114 and the outer implant surface 112. The hole axis 120 can be oriented relative to the thickness axis 118 at an angle θ. In some embodiments, the angle θ may range between about zero (0) to about fifteen (15) degrees. However, the angle θ may be more fifteen (15) degrees. The holes 106 may have different hole axes 120 having different angulations. For instance, some holes 106 may define hole axes 120 that are oriented at an oblique angle relative to the thickness axes, whereas other holes 106 may define hole axes 120 that are substantially parallel to the thickness axis 118. The angulation of the holes 106 relative to the thickness axes 118 may depend on a number of factors. For instance, the surgeon may desire to orient a specific hole 106 at a particular angle relative to the thickness axis 118 such that a fastener 108 inserted through that hole 106 does not contact nerves, teeth, or any other desired tissue portion of the tissue body 10. Moreover, the surgeon may desire to orient two or more adjacent holes 106 at specific angles relative to the thickness axis 118 such that, when fasteners 108 are inserted into these holes 108, the fasteners 108 do not interfere with one another (see FIG. 1D).

The implant body 104 may have internal implant surfaces 122 corresponding to each hole 106. Each internal implant surface 122 defines one of the holes 106. Some or all of the holes 106 can be threaded. Therefore, some or all of the holes 106 may include internal implant threads 124 that are configured to mate with external threads of the fastener 108 so that the fastener 108 can be coupled to the implant body 104. Some or all of the holes 106 may not have internal threads.

The patient specific orthopedic implant 100 may be substantially shaped to match the shape of an outer contour of the tissue body 10. In the depicted embodiment, the patient specific orthopedic implant 100 can be designed to be coupled to one side of the mandible 16. To this end, the implant body 104 may include a first implant portion 126 and a second implant portion 128 that is angularly offset from the first implant portion 126 (FIG. 2A). The first implant portion 126 can be configured to fit over an anterior surface of the mandible 16. Moreover, the first implant portion 126 can be connected to the second implant portion 128 at an angular offset. In the depicted embodiment, the first implant portion 126 can be offset relative to the second implant portion 128 at an oblique angle. The second implant portion 128 can be configured to fit over a lateral surface of the mandible 16. The implant body 104 may further include a third implant portion 130 that is angularly offset from the first implant portion 126 and the second implant portion 128. The third implant portion 130 can be connected to the second implant portion 128 at an angular offset. In the depicted embodiment, the third implant portion 130 can be angularly offset relative to the second implant portion 128 at an oblique angle. Moreover, the third implant portion 130 can be configured to fit over at least a portion of the ramus of the mandible 16.

FIG. 3A shows another embodiment of a patient specific orthopedic implant 200 that is similar to the patient specific orthopedic implant 100 described above. The patient specific implant 200 can be configured as a bone plate 202 and includes an implant body 204 that is made from a suitable biocompatible material. Suitable biocompatible materials include, but are not limited to, cobalt chromium molybdenum (CoCrMo), titanium, and titanium alloys, stainless steel, ceramics, or polymers such as polyetheretherketone (PEEK), polyetherketoneketone (PEKK), and bioresorbable materials. The patient specific implant 200 may further define a plurality of holes 206 that extend through the implant body 204. The holes 206 can be substantially similar to the holes 106 of the patient specific implant 100 described above. Thus, the holes 206 are configured to receive fasteners 108. The implant body 204 can be designed to fit over most of the mandible 12. To this end, the implant body 204 may include a first implant portion 226 and a second implant portion 228 that is angularly offset from the first implant portion 226. The first implant portion 226 can be configured to fit over at least a portion of the ramus of the mandible 16. Moreover, the first implant portion 226 can be connected to the second implant portion 228 at an oblique angle. The second implant portion 228 can be configured to fit over a lateral surface of the mandible 16. The implant body 204 can further include a third implant portion 230 that is connected to the second implant portion 228. The third implant portion 230 can be configured to fit over an anterior surface of the mandible 16. Further, the third implant portion 230 can be angularly offset from the second implant portion 228. The implant body 204 includes a fourth implant portion 232 that is connected to the third implant portion 230. The fourth implant portion 232 can be configured to fit over a lateral surface of the mandible 16. Moreover, the fourth implant portion 232 can be angularly offset from the third implant portion 230. The implant body 204 includes a fifth implant portion 234 that is connected to the fourth implant portion 232. The fifth implant portion 234 can be configured to fit over at least a portion of the ramus of the mandible 16. Further, the fifth implant portion 234 can be angularly offset from the fourth implant portion 232. In the orthopedic arts, the patient specific orthopedic implant 200 is referred to as the double-angled implant.

FIG. 3B illustrates another embodiment of a patient specific implant 300. The patient specific implant 300 can be configured to fit over an anterior portion and parts of the two lateral portions of the mandible 16. In the depicted embodiment, the patient specific implant 300 can be configured as a bone plate 302 and includes an implant body 304. The patient specific implant 300 defines holes 306 that extend through the implant body 304. The holes 306 can be configured to receive fasteners 108. The holes 306 can be substantially similar to the holes 106 described above. The implant body 304 includes a first implant portion 326 and a second implant portion 328 that is connected to the first implant portion 326. The first implant portion 326 is configured to fit over a lateral portion of the mandible 16 and is angular offset relative to the first implant portion 326. The second implant portion 328 can fit over an anterior surface of the mandible 16. The implant body 304 can further include a third implant portion 330 that is connected to the second implant portion 328. The second implant portion 328 can be angularly offset relative to the second implant portion 328 and can be configured to fit over a lateral portion of the mandible 16.

Figure 4:
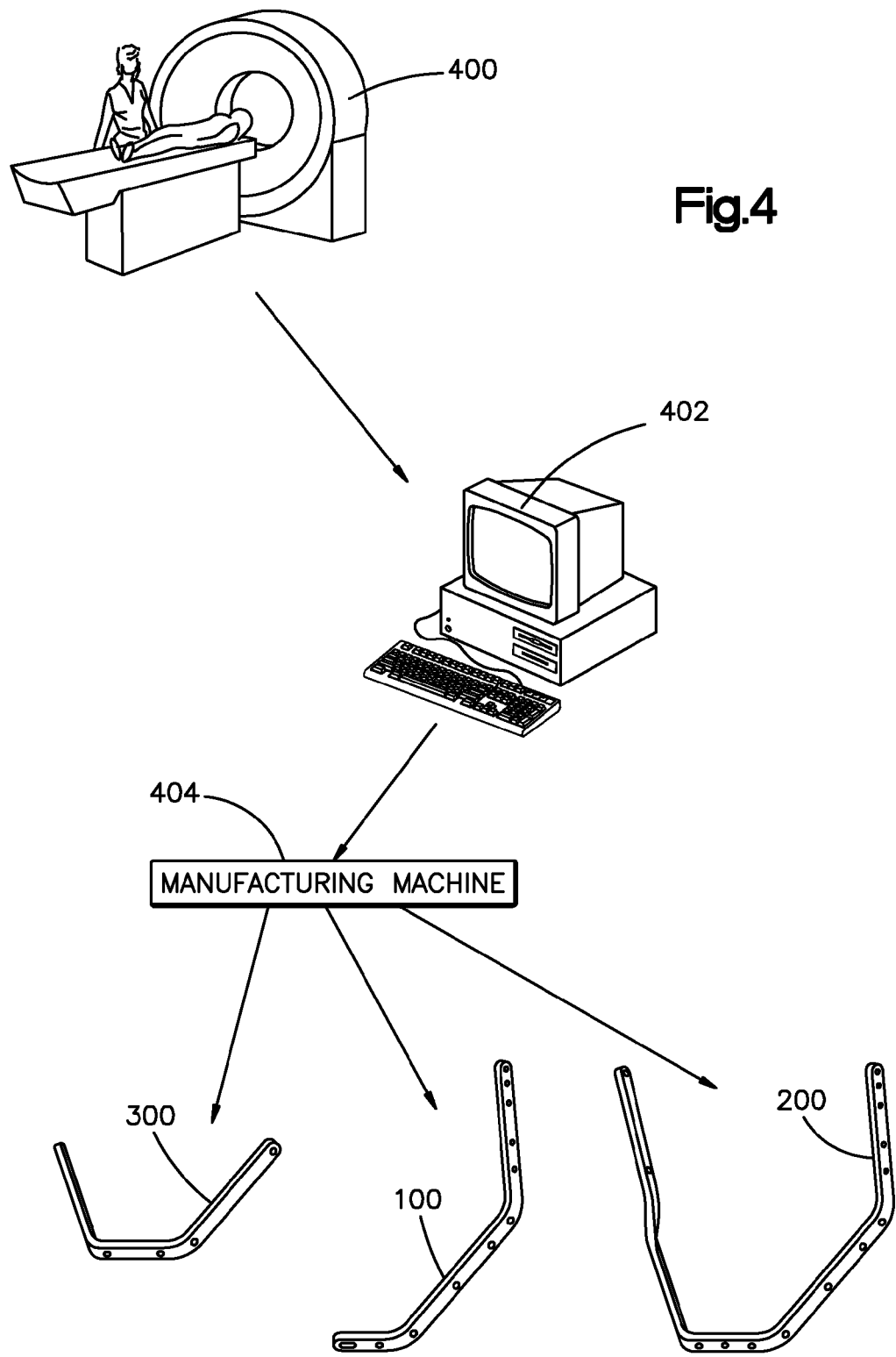
FIG. 4 shows a method of making the patient specific orthopedic implants shown in FIGS. 2A-C and 3A-B.

FIG. 4 illustrates a method of making any of the patient specific orthopedic implants described above. In the interest of brevity, this method is described in relation to the patient specific orthopedic implant 100. However, the method can be used to make any of the patient specific orthopedic implants described above. This method may include some or all of the steps described below. The patient specific orthopedic implant 100 can be manufactured pre-operatively. Before commencing the appropriate surgery, a virtual three-dimensional image of the tissue body 10 using any suitable technology is obtained. The virtual three-dimensional image of the tissue body 10 can be obtained by scanning the tissue body 10 using a scanning machine 400 that is suitable to scan anatomical tissue. For example, the virtual three-dimensional image of the mandible 16 can be obtained using the scanning machine 400. The scanning machine 400 can be a computed tomography (CT) scan machine, a laser scanning machine, an optical scanning machine, a magnetic resonance imaging (MRI) machine, a coordinate measuring machine or any other machine or device capable of scanning the tissue body 10. Specifically, the scanning machine 400 can be used to scan the tissue body 10. Regardless of the scanning methodology employed, a virtual three-dimensional image of the tissue body 10 is obtained. This image includes images of the tunnels that receive the nerves. Accordingly, the location of the nerves in the tissue body 10 can be identified.

Once the virtual three-dimensional image of the tissue body 10 is obtained, the image data obtained by the scanning machine 400 can then be downloaded or transferred to a computing device 402 to create a virtual three-dimensional model of the tissue body 10. The computing device 402 can be local (i.e., in the same general area as the scanning machine 400) or remote where the image should be transmitted via a network. The computing device 402 includes a processor that is capable of manipulating image data. In addition to the processor, the computing device 402 may include a non-transitory computer-readable storage medium that is capable of storing image data. Alternatively, the computing device 402 may not include a non-transitory computer-readable storage medium; rather, the computing device 402 may be coupled to a non-transitory computer-readable storage medium. In event, the computing device 402 can run a computer-aided design software.

A virtual three-dimensional model of an orthopedic implant, such as the orthopedic implant 100, can be obtained. The virtual three-dimensional model of the orthopedic implant 100 can be composed of data that can be manipulated by a processor and that can be read by a non-transitory computer-readable medium. This data can be in different formats. For example, the virtual three-dimensional model of the orthopedic implant 100 can include data in a Standard Tessellation Language (STL) format. Irrespective of the data format, the virtual three-dimensional model of the orthopedic implant 100 includes data that maps the shape, contour, and size of the orthopedic implant 100. The virtual three-dimensional model of the orthopedic implant 100 can be created virtually in a computer. In the computing device 402 or another computing device, the virtual three-dimensional model of the orthopedic implant 100 is designed so that is contoured and shaped to fit over a particular portion of the virtual three-dimensional model of the tissue body 10. For example, the virtual three-dimensional model of the orthopedic implant 100 can be shaped and contoured to fit over an anterior surface and a lateral surface of the mandible 16. The virtual three-dimensional models of the orthopedic implant 100 and the tissue body 10 can be manipulated using a suitable software such as the software sold under the trademark PROPLAN CMF® by Synthes.

The virtual three-dimensional model of the orthopedic implant 100 is then processed so as to create one or more holes 106. The user such as a surgeon can determine the angulation and position of the holes 106 in accordance with a predetermined surgical plan. Specifically, the virtual three-dimensional model of the orthopedic implant 100 can be manipulated so that the holes 106 are positioned relative to the implant body 104 such that the fasteners 108 do not extend into a predetermined section of the tissue body 10 when the fasteners are at least partially disposed in the holes 106. For example, the virtual three-dimensional model of the orthopedic implant 100 can be manipulated so that the holes 106 are positioned along the implant body 104 so that the fasteners 108 would not contact nerves or teeth of the tissue body 10. Similarly, the virtual three-dimensional model of the orthopedic implant 100 can be manipulated so that the holes 106 are angled relative to the implant body 104 so that the fasteners 108 would not contact nerves, teeth, and/or dental implants of the tissue body 10. The holes 106 can be positioned or aligned so that the fasteners 108 would not contact any type of hardware such as a dental implant. The user can also manipulate the virtual three-dimensional model of the orthopedic implant 100 to adjust the position and/or angulation of the holes 106 such that the fasteners 108 do not contact one another when the fasteners 108 as illustrated in FIG. 1D. In determining the proper position and/or angulation of the holes 106 with respect to the implant body 104, the user may select the fasteners 108 with the appropriate length so that the fasteners 108 do not interfere with one another when the fasteners 108 are inserted in the holes 106. It is envisioned that the virtual three dimensional models of the fasteners 108 can be obtained. The virtual three-dimensional models of the fasteners 108 can be inserted through the holes 108 of the virtual three-dimensional model of the orthopedic implant 100 to determine whether the fasteners 108 extend into nerves, teeth, or interfere with one another. If the virtual three-dimensional models of the fasteners 108 interfere with nerves, teeth, or each other, the position or angulation of the holes 108 of the virtual three-dimensional model of the orthopedic implant 100 can be manipulated. It is envisioned that the surgeon may manipulate the virtual three-dimensional model of the orthopedic implant 100 before the surgery to reduce the amount of time that is spent in the operating room adjusting the orthopedic implant 100 so that it fits the particular patient. Since the operating room time is reduced, the duration of the anesthesia can be reduced as well.

Once the virtual three-dimensional model of the orthopedic implant 100 has been completed, the orthopedic implant 100 can be created using any suitable technology. The completed virtual three-dimensional model of the orthopedic implant 100 can be downloaded or transferred from the computing device 402 to a manufacturing machine 404 such as a CAD/CAM manufacturing machine. The completed virtual three-dimensional model of the orthopedic implant 100 can be transferred or downloaded directly from the computing device 402 to the manufacturing machine 404 or from the computing device 402 to another computer and then to the manufacturing machine 404. The manufacturing machine 404 can be a computer numerical control (CNC) machine. A suitable software can be used to generate CNC code from the data that represents the virtual three-dimensional model of the orthopedic implant 100. For example, a software sold under the trademark SYNOPSIS™ by CADS GmbH can be used to generate the CNC code from the virtual three-dimensional model of the orthopedic implant 100. The software can generate CNC code in any suitable programming language. For instance, the SYNOPSIS or any other suitable software can generate CNC code in G-code or STEP-NC programming languages. The CNC code can then be downloaded or transferred to the CNC machine so that the CNC machine can manufacture the patient specific orthopedic implant 100.

It is envisioned that the methods described above can used not only to manufacture the orthopedic implants described herein but also other orthopedic implants or guiding implant. For instance, the method described herein can be used to manufacture the bone fixation implant and the osteotomy guiding implant that are described in U.S. Patent Application Publication No. 2012/0029574, filed on Apr. 1, 2011, the entire disclosure of which is incorporated herein by reference. Furthermore, the methods described herein can used to manufacture and customize the bone fixation device, bone plate, and aiming guide that are described in U.S. patent application Ser. No. 13/426,079 filed on Mar. 21, 2012, the entire disclosure of which is incorporated by reference.

It should be noted that the illustrations and discussions of the embodiments shown in the figures are for exemplary purposes only, and should not be construed limiting the disclosure. One skilled in the art will appreciate that the present disclosure contemplates various embodiments. For example, although the present disclosure refers to virtual three-dimensional models, it is envisioned that any of the virtual models described in the present disclosure can be two-dimensional. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed is:

1. A method, comprising:
   obtaining a virtual three-dimensional model of a tissue body;
   designing, via a software program executed by a computing device, a virtual three-dimensional model of an orthopedic implant that includes an implant body such that the virtual three-dimensional model of the orthopedic implant is contoured to fit over a particular portion of the virtual three-dimensional model of the tissue body, the implant body being elongate along a longitudinal axis, the implant body including at least one hole that extends along a hole axis that is angled with respect to the longitudinal axis of the implant body;
   manipulating, via the software program, the virtual three-dimensional model of the orthopedic implant to overlay the particular portion of the virtual three-dimensional model of the tissue body so as to define a manipulated virtual three-dimensional model of the orthopedic implant;

inserting, via the software program, a virtual three-dimensional model of a fastener at least partially into the at least one hole of the implant body so that the virtual three-dimensional model of the fastener does not extend into a predetermined section of the obtained virtual three-dimensional model of the tissue body, wherein the predetermined section of the obtained virtual three-dimensional model of the tissue body includes a nerve, a tooth, or hardware; and transferring the manipulated virtual three-dimensional model of the orthopedic implant to a manufacturing machine, wherein the manufacturing machine is configured to construct a patient specific orthopedic implant that corresponds to the manipulated virtual three-dimensional model of the orthopedic implant.

2. The method according to claim 1, wherein the predetermined section is an intersection with another fastener that extends through the implant body.

3. The method according to claim 1, wherein the tissue body is a mandible and the obtaining step includes obtaining a virtual three-dimensional model of the mandible.

4. The method according to claim 1, wherein the tissue body is a maxilla and the obtaining step includes obtaining a virtual three-dimensional model of the maxilla.

5. The method according to claim 1, wherein the obtaining step includes scanning the tissue body using a scanning machine selected from the group consisting of a computed tomography (CT) scan machine, a laser scanning machine, an optical scanning machine, a magnetic resonance imaging (MRI) machine, and a coordinate measuring machine.

6. The method according to claim 1, wherein the at least one hole is a first hole, the virtual three-dimensional model of the fastener is a virtual three-dimensional model of a first fastener, and the method comprises the step of designing a second hole that extends through the implant body such that second hole is positioned or angled with respect to the implant body so that a virtual three-dimensional model of a second fastener does not contact the virtual three-dimensional model of the first fastener when the virtual three-dimensional models of the first and second fasteners are at least partially disposed in the first and second holes of the manipulated virtual three-dimensional model of the orthopedic implant, respectively.

7. The method according to claim 1, further comprising constructing the patient specific orthopedic implant to correspond to the manipulated virtual three-dimensional model of the orthopedic implant using the manufacturing machine.

8. The method of claim 7, further comprising generating a CNC code using data that represents the manipulated virtual three-dimensional model of the orthopedic implant and the at least one hole.

9. The method of claim 8, wherein the constructing step includes transferring the CNC code to a CNC machine.

10. The method of claim 9, wherein the constructing step includes constructing the patient specific orthopedic implant using the CNC machine.

11. The method according to claim 1, wherein the manipulating step includes coupling the virtual three-dimensional model of the orthopedic implant to the virtual three-dimensional model of the tissue body.

12. The method of claim 1, further comprising programming the manufacturing machine to construct the patient specific orthopedic implant that corresponds to the manipulated virtual three-dimensional model of the orthopedic implant.

13. The method of claim 1, wherein after the inserting step, redesigning the manipulated virtual three-dimensional model of the orthopedic implant if the virtual three-dimensional model of the fastener extends into the predetermined section of the obtained virtual three-dimensional model of the tissue body.

14. The method of claim 13, wherein the redesigning step includes adjusting a position or angulation of the at least one virtual hole of the manipulated virtual three-dimensional model of the orthopedic implant.

15. A method, comprising:

designing, via a software program executed by a computing device, a virtual three-dimensional model of an orthopedic implant that is contoured to fit over a predetermined portion of a virtual three-dimensional model of a tissue body, the virtual three-dimensional model of the orthopedic implant including an implant body that is elongate along a longitudinal axis, and at least one virtual hole that extends through the implant body of the virtual three-dimensional model of the orthopedic implant along a hole axis that is angled with respect to the longitudinal axis of the implant body;

manipulating, via the software program, the virtual three-dimensional model of the orthopedic implant to overlay the predetermined portion of the virtual three-dimensional model of the tissue body so as to define a manipulated virtual three-dimensional model of the orthopedic implant;

inserting, via the software program, a virtual three-dimensional model of a fastener at least partially into the at least one virtual hole of the implant body so that the virtual three-dimensional model of the fastener does not extend into a predetermined section of the obtained virtual three-dimensional model of the tissue body, wherein the predetermined section of the obtained virtual three-dimensional model of the tissue body includes a nerve, a tooth, or hardware; and transferring the manipulated virtual three-dimensional model of the orthopedic implant to a manufacturing machine, wherein the manufacturing machine is configured to construct a patient specific orthopedic implant that corresponds to the manipulated virtual three-dimensional model of the orthopedic implant.

16. The method of claim 15, further comprising obtaining the virtual three-dimensional model of the tissue body.

17. The method of claim 16, wherein the obtaining step includes scanning the tissue body using a scanning machine.

18. The method of claim 16, wherein, in the obtaining step, the scanning machine is selected from a group consisting of a computed tomography (CT) scan machine, a laser scanning machine, an optical scanning machine, a magnetic resonance imaging (MRI) machine, and a coordinate measuring machine.

19. The method of claim 16, wherein, in the obtaining step, the tissue body is a mandible, and the obtaining step further includes scanning the mandible using the scanning machine.

20. The method of claim 15, further comprising constructing a physical orthopedic implant to correspond to the manipulated virtual three-dimensional model of the orthopedic implant using the manufacturing machine.

21. The method of claim 20, further comprising generating a CNC code using data that represents the virtual three-dimensional model of the orthopedic implant and the at least one virtual hole.

22. The method of claim 21, wherein the constructing step includes transferring the CNC code to a CNC machine.

23. The method of claim 22, wherein the constructing step include constructing the physical orthopedic implant using the CNC machine.

24. The method of claim 15, wherein the at least one virtual hole is a first virtual hole, the virtual three-dimensional model of the fastener is a virtual three-dimensional model of a first fastener, and the method comprises the step of designing a second virtual hole such that the second virtual hole is positioned and angled with respect to the implant body so that a virtual three-dimensional model of a second fastener does not interfere with the virtual three-dimensional model of the first fastener when the virtual three-dimensional models of the first and second fasteners are at least partially disposed in the first and second virtual holes of the manipulated virtual three-dimensional model of the orthopedic implant, respectively.

25. The method of claim 15, wherein the designing step includes obtaining location data that includes information about an angle or position of the at least one virtual hole relative to the implant body.

26. The method of claim 15, further comprising programming the manufacturing machine to construct the patient specific orthopedic implant that corresponds to the manipulated virtual three-dimensional model of the orthopedic implant.

27. The method of claim 15, wherein after the inserting step, redesigning the manipulated virtual three-dimensional model of the orthopedic implant if the virtual three-dimensional model of the fastener extends into the predetermined section of the obtained virtual three-dimensional model of the tissue body.

28. The method of claim 27, wherein the redesigning step includes adjusting a position or angulation of the at least one virtual hole of the manipulated virtual three-dimensional model of the orthopedic implant.

\* \* \* \* \*